United States Patent [19]

Waespe et al.

[11] Patent Number: 5,369,084
[45] Date of Patent: Nov. 29, 1994

[54] ISONICOTINIC ACID DERIVATIVES AND RELATED SPIRO COMPOUNDS WITH HERBICIDAL ACTION

[75] Inventors: Hans-Rudolf Waespe, Allschwil, Switzerland; Guy R. E. Van Lommen, Berlaar; Victor K. Sipido, Merksem, both of

[73] Assignee: Janssen Pharmaceutical N.V., Beerse,

[21] Appl. No.: 50,269

[22] Filed: May 6, 1993

[30] Foreign Application Priority Data

Nov. 22, 1990 [CH] Switzerland .................. 3695/90
Jan. 24, 1991 [CH] Switzerland .................. 00211/91

[51] Int. Cl.$^5$ .................. A01N 43/40; A01N 43/90; C07D 213/78; C07D 491/048
[52] U.S. Cl. .................. 504/244; 504/245; 504/246; 504/251; 504/252; 504/289; 504/292; 504/297; 504/298; 546/18; 546/113; 546/114; 546/115; 546/269; 546/274; 546/323; 546/326; 540/586; 540/593
[58] Field of Search .................. 504/245, 219, 244, 245, 504/246, 251, 284, 288, 289, 292, 297, 298; 546/79, 113, 114, 115, 269, 274, 323, 326, 18; 540/586, 593; A01N 43/40

[56] References Cited

U.S. PATENT DOCUMENTS 3,544,303  12/1970  Swidler et al. .................. 504/245

FOREIGN PATENT DOCUMENTS 257265   9/1967  Austria .
0316491  5/1989  European Pat. Off. .
0322616  7/1989  European Pat. Off. .
898322   6/1962  United Kingdom .

OTHER PUBLICATIONS

Epsztajn et al., "Applications of Organolithium and Related Reagents in Synthesis. Part 4. A general Study of the Reactions of N,N-dialkylpyridinecarboxamides with Lithium Di-isopropylamide", *J. Chem. Research (S)*, 1986, 18–19.
Meyers et al., "Substitutions on Pyridines Activated by Oxazolines via Nucleophilic Additions or Metalation–Alkylation", *J. Org. Chem.*, 1982, 47, 2633–2637.
Epsztajn et al., "Reactions of the N,N–Dialkylpyridylcarboxylic Amides with Lithium Amides. Regioselective Lithiation of N,N–Diisopropylpyridylcarboxylic Amides, A Useful Method for Synthesis of 2,3–and 3,4–Disubstituted Pyridines", *Tetrahedron Letters*, vol. 21, pp. 4739–4742.

*Primary Examiner*—Richard L. Raymond
*Assistant Examiner*—S. Mark Clardy
*Attorney, Agent, or Firm*—Charles J. Metz

[57] ABSTRACT

Isonicotinic acid derivatives and related furo-, thieno- and pyrrolo[3,4-c]pyridin-1(3H)-one, -thione and -imine compounds having the formula

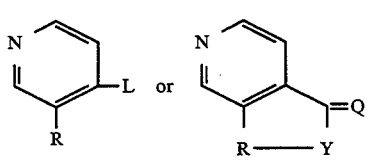

(I)

wherein R is

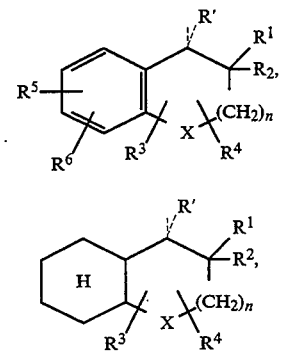

(Abstract continued on next page.)

-continued
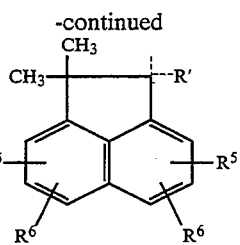
-continued
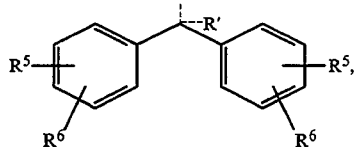
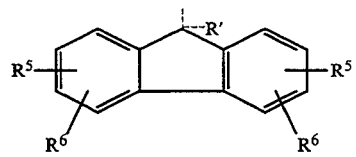
or
Q is O, S or $NR^7$; Y is O, S or $NR^8$; L is $COOR^9$, $CONR^{10}R^{11}$, $C(=S)NR^{10}R^{11}$, CN, or a radical of formula
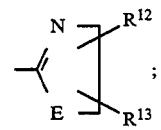
the acceptable addition salts, the stereochemically isomeric forms and the N-oxides thereof, having herbicidal properties, compositions containing the same and methods for controlling weeds.
24 Claims, No Drawings

ISONICOTINIC ACID DERIVATIVES AND RELATED SPIRO COMPOUNDS WITH HERBICIDAL ACTION

CROSS-REFERENCE TO RELATED APPLICATIONS

This application is based upon PCT Application No. PCT/EP91/02142, filed Nov. 12, 1991, which claims priority from Swiss Application Ser. No. 3695/90-6, filed Nov. 22, 1990, and Swiss Application Ser. No. 00211/91-5, filed Jan. 24, 1991.

BACKGROUND OF THE INVENTION

In J. Chem. Research (S), 1986, 18–19 there are disclosed 3,3-diphenyl-3H-furo[3,4-c]pyridin-1-one and 3-(diphenylhydroxymethyl)-N,N-bis(1-methylethyl)-4-pyridine carboxamides as end products in a study of new organolithium reagents for use in synthesis.

The present invention is concerned with novel herbicidally active isonicotinic acid derivatives and related furo-, thieno- and pyrrolo[3,4-c]pyridine-1(3H)-one, -thione and -imine compounds, compositions containing these compounds as active ingredients, and a method for controling weeds, preferably selectively in crops of useful plants. Further the invention also relates to a process for making these novel compounds.

DESCRIPTION OF THE INVENTION

The present invention is concerned with herbicidally active isonicotinic acid derivatives and related furo-, thieno- and pyrrolo[3,4-c]pyridin-1(3H)-one, -thione and -imine compounds having the formula

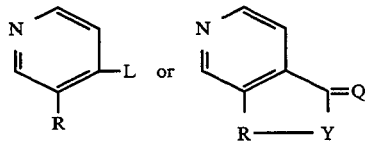

the acceptable addition salts, the stereochemically isomeric forms and the N-oxides thereof, wherein R is attached to the pyridinyl group by a single bond or by a spiro-bond, and R has the formula

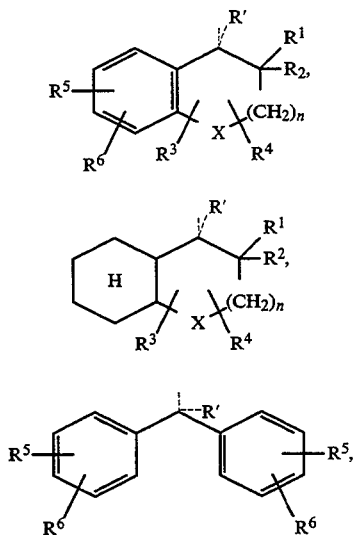

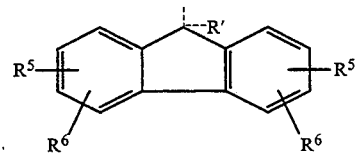

or

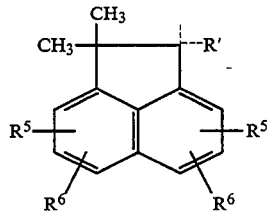

wherein
R' is hydrogen, fluoro, hydroxy or a spiro-bond;
$R^1$ and $R^2$ are each independently hydrogen, $C_{1-6}$alkyl or $R^1$ and $R^2$ together with the carbon atom to which they are connected form a spiro $C_{3-6}$cycloalkyl group; or R' and $R^1$ form an extra bond;
$R^3$ and $R^4$ are each independently hydrogen or $C_{1-6}$alkyl;
$R^5$ and $R^6$ are each independently hydrogen, halo, $C_{1-4}$alkyl, $C_{1-4}$alkyloxy, $C_{1-4}$haloalkyloxy, $C_{1-4}$haloalkyl, $C_{3-7}$alkenyl, amino, carbonyl, nitro, methoxycarbonyl or aminocarbonyl;
Q is O, S or $NR^7$;
X is $CH_2$, O, S, SO or $NR^8$;
Y is O, S or $NR^8$;
n is 0, 1 or 2;
L is $COOR^9$, $CONR^{10}R^{11}$, $C(=S)NR^{10}R^{11}$, CN, or a radical of formula

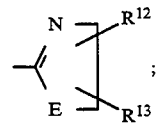

E is O, S or $NR^8$;
$R^7$ is 1,1-dimethyl-2-hydroxyethyl or 2-methyl-2-fluoropropyl;
$R^8$ is hydrogen, $C_{1-6}$alkyl or 1,1-dimethyl-2-hydroxyethyl;
$R^9$ is hydrogen, $C_{1-7}$alkyl, $C_{3-8}$alkenyl, $C_{3-8}$alkynyl, $C_{2-16}$alkyloxyalkyl or $C_{3-7}$cycloalkyl;
$R^{10}$ is hydrogen, $C_{1-3}$alkyl or 1,1-dimethyl-2-hydroxyethyl;
$R^{11}$ is hydrogen, $C_{1-3}$alkyl or phenyl; and
$R^{12}$ and $R^{13}$ each independently are hydrogen or methyl.

The isonicotinic acid derivatives and the related furo-, thieno- and pyrrolo[3,4-c]pyridin-1(3H)one, -thione and -imine compounds of formula (I) are novel, except for 3,3-diphenyl-3H-furo[3,4-c]pyridin-1-one and 3-(diphenylhydroxymethyl)-N,N-bis(1-methylethyl)-4-pyridinecarboxamide described in J. Chem. Research (S), 1986, p. 18–19. Suprisingly, the compounds of formula (I) exhibit strong herbicidal properties and are therefore useful to control weeds. This property gains importance by the fact, that some crops of useful plants are not damaged, or are only slightly harmed at high dosages when treated with compounds of formula (I). Consequently, the compounds of formula (I) are valuable selective herbicides in crops of useful plants, such as sugar beet, rape, soybeans, cotton, sunflower, cereals, especially wheat, barley, rye and oats, rice, both upland rice and paddy rice, and maize. Especially in rice crops a broad range of application rates can be employed, preferably if the rice crops are transplanted rice crops, and if the compounds of formula (I) are applied after transplantation.

The active ingredients (a.i.) of formula (I) are usually applied at application rates of 0.01 to 5.0 kg of active ingredient per hectare in order to achieve satisfying results. Sometimes, depending on the environmental conditions, the application rates may exceed the above designated limitations. However, the preferred application rates are between 0.05 kg and 1.0 kg a.i. per hectare.

As used in the foregoing definitions alkyl denotes straight or branch chained saturated hydrocarbon radicals, e.g. methyl, ethyl, n.propyl, isopropyl, the butyl, pentyl, hexyl or heptyl isomers; alkyloxy defines methyloxy, ethyloxy, propyloxy or the four butyloxy isomers, with methyloxy, ethyloxy or isopropyloxy being preferred; halo is generic to fluoro, chloro, bromo or iodo, with fluoro and chloro being preferred; alkenyl defines e.g. ethenyl, 2-propenyl, 1-methylethenyl, 3-butenyl, 2-butenyl, 1-butenyl, 1-propenyl, methyl-2-propenyl or 3-methyl-2-butenyl, with ethenyl, 2-propenyl and methyl-2-propenyl being preferred; alkynyl denotes e.g. ethynyl, 1-propynyl, propargyl, 1-butynyl, 2-butynyl or 3-butynyl, with ethynyl or propargyl being preferred; cycloalkyl defines cyclopropyl, cyclobutyl, cyclopentyl, cyclohexyl or cycloheptyl, with cyclopentyl or cyclohexyl being preferred. Radicals that can be obtained from combination of groups defined hereinabove e.g. haloalkyl, alkyloxyalkyl or haloalkylcarbonyl are defined by the combination of the corresponding group member definitions. Important examples thereof are trifluoromethyl, chloromethyl, 2,2,2-trifluoroethyl, methoxymethyl, methoxyethyl or ethoxyethyl.

The $R^1$ and $R^2$ radicals attached to the same carbon atom. Hence, $R^1$ and $R^2$ together with this carbon atom may form a spiro-ring structure. A typical example of such spiro-rings are cyclopropane, cyclopentane, cyclohexane and cycloheptane.

The invention also comprises the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

Examples of salt-forming mineral acids are hydrofluoric acid, hydrochloric acid, hydrobromic acid, hydroiodic acid, sulfuric acid, nitric acid, chloric acid, perchloric acid or phosphoric acid. Preferred salt-forming sulfonic acids are toluenesulfonic acid, benzenesulfonic acid, methanesulfonic acid or trifluoromethane sulfonic acid. Preferred salt-forming carboxylic acids are acetic acid, trifluoroacetic acid, benzoic acid, chloroacetic acid, phthalic acid, maleic acid, malonic acid and citric acid. Phosphorus containing acids are the various phosphonous acids, phosphonic acids and phosphinic acids.

Preferred salt-forming alkali metal hydroxides and earth alkaline metal hydroxides are the hydroxides of lithium, sodium, potassium, magnesium or calcium, most preferably those of sodium or potassium. Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine, diethanolamine and 1,4-diazabicyclo[2.2.2]octane being most preferred. Examples of quaternary ammonium bases are, in general, the cations of haloammonium salts, e.g. the tetramethylammonium cation, the trimethylbenzylammonium cation, the triethylbenzylammonium cation, and also the ammonium cation.

The invention also comprises all steroisomers of the compounds of formula (I). Unless otherwise mentioned or indicated, the chemical designation of compounds denotes the mixtures of all stereochemically isomeric forms. These mixtures contain all diastereomers and enantiomers of the basic molecular structure.

Pure isomeric forms of these compounds can be separated from the mixtures by conventional separation methods. Enantiomers, for example, can be separated by liquid chromatography over a chiral stationary phase.

Interesting compounds are those compounds of formula (I), wherein $R^1$ and $R^2$ are each independently hydrogen, $C_{1-6}$alkyl or $R^1$ and $R^2$ together with the carbon atom to which they are connected form a spiro $C_{3-6}$cycloalkyl group; Q is O or S; n is 0 or 1; L is $COOR^9$, $CONR^{10}R^{11}$, CN, or a radical of formula

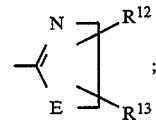

$R^8$ is hydrogen or $C_{1-6}$alkyl; $R^{10}$ is hydrogen or $C_{1-3}$alkyl; $R^{11}$ is hydrogen or $C_{1-3}$alkyl; and $R^{13}$ is hydrogen.

Preferred compounds are those compounds of formula (I) wherein R represents

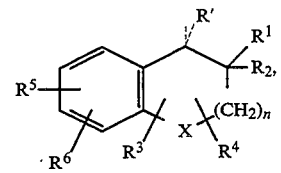

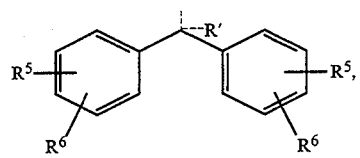

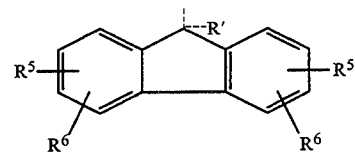

or

-continued

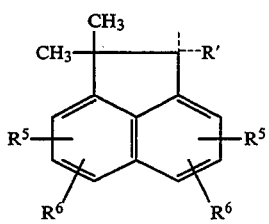

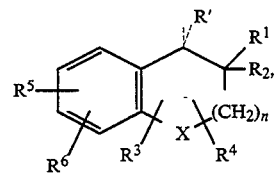

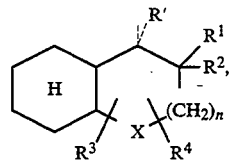

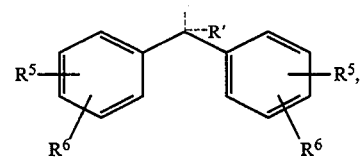

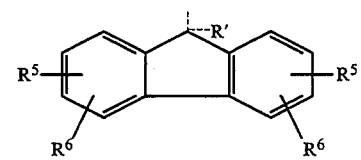

or

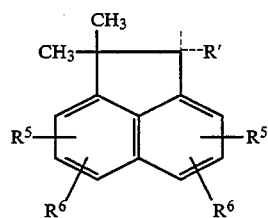

wherein R' is hydrogen, fluoro, hydroxy or a spiro-bond; $R^1$ and $R^2$ are each independently hydrogen, $C_{1-6}$alkyl or $R^1$ and $R^2$ together with the carbon atom to which they are connected form a spiro $C_{3-6}$cycloalkyl group; or R' and $R^1$ form an extra bond; $R^3$ and $R^4$ are each independently hydrogen or $C_{1-6}$alkyl; $R^5$ and $R^6$ are hydrogen; Q is O, S or $NR^7$; X is $CH_2$, O or S; Y is O or $NR^8$; n is 0 or 1; L is $COOR^9$, $CONR^{10}R^{11}$ or $C(=S)NR^{10}R^{11}$; $R^7$ is 1,1-dimethyl-2-hydroxyethyl or 2-methyl-2-fluoropropyl; $R^8$ is hydrogen, $C_{1-6}$alkyl or 1,1-dimethyl-2-hydroxyethyl; $R^9$ is hydrogen or $C_{1-7}$alkyl; $R^{10}$ is hydrogen, $C_{1-3}$alkyl or 1,1-dimethyl-2-hydroxyethyl; and $R^{11}$ is hydrogen, $C_{1-3}$alkyl or phenyl.

Particularly preferred compounds are those preferred compounds wherein R' is hydrogen or a spiro-bond; $R^1$ and $R^2$ are each independently hydrogen or $C_{1-4}$alkyl; $R^3$ and $R^4$ are each independently hydrogen or $C_{1-4}$alkyl; Q is O; X is $CH_2$ or O; Y is O or NH; L is $COOR^9$ or $CONR^{10}R^{11}$; $R^9$ is hydrogen or $C_{1-4}$alkyl; $R^{10}$ is hydrogen or $C_{1-3}$alkyl; and $R^{11}$ is hydrogen or $C_{1-3}$alkyl.

The most preferred compounds are those compounds wherein R represents

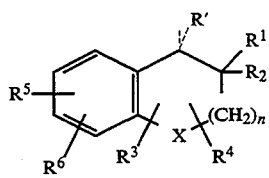

wherein R' is hydrogen or a spiro-bond; $R^1$ and $R^2$ are each independently hydrogen or $C_{1-4}$alkyl; $R^3$ and $R^4$ are each independently hydrogen or $C_{1-4}$alkyl; Q is O; X is $CH_2$; Y is O or NH; and L is $COOCH_3$.

The most interesting compound of formula (I) is methyl 3-(2,3-dihydro-2,2-dimethyl-1H-inden-1-yl)-4-pyridinecarboxylate.

The compounds of formula (I) comprise the isonicotinic acid derivatives of formula (I-a)

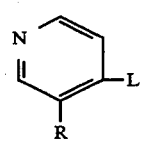

(I-a)

wherein R is a radical of the formula and wherein R' is hydrogen, fluoro or hydroxy, and X, n, L, and $R^1$ to $R^9$ are as defined under formula (I). Typical examples are e.g.

3-(2,2-dimethyl-1-indanyl)isonicotinic acid, 3-(2,2-dimethyl-1-indanyl)isonicotinic acid methyl ester, 3-(2,2-dimethyl-1-indanyl)isonicotinic acid (1,1-dimethyl-2-hydroxyethyl)amide, 3-(2,2-dimethyl-1-indanyl)isonicotinic acid (1,1-dimethyl-2-hydroxyethyl)amide hydrochloride, 3-[2,2-dimethyl-1-(1,2,3,4-tetrahydronaphthyl-)isonicotinic acid methyl ester, 3-[2,3-dimethyl-1-(3,4-dihydronaphthyl)]isonicotinic acid methyl ester, 3-diphenylmethyl-isonicotinic acid, 3-diphenylmethyl-isonicotinic acid methyl ester, and 3-diphenylmethyl-isonicotinic acid (1,1-dimethyl-2-hydroxyethyl)amide.

The compounds of formula (I) also comprise furo- and thieno[3,4-c]pyridin-1(3H)-one, -thione and -imine derivatives having the formula (I-b)

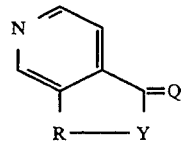 (I-b)

wherein Q and R are as defined under formula (I) and Y is O or S.

Preferred compounds represented by formula (I-b) are:

spiro[1-(2,2-dimethyl)indanyl]-1,3'(1'H̲)-furo[3,4-c]pyridin-2'-one;

spiro[1-(2,2-dimethyl-1,2,3,4-tetrahydronaphthyl)]-1,3'(1'H̲)-furo[3,4-c]pyridin-2'-one;

spiro[1-(2,2-dimethyl)indanyl]-1,3'(1'H̲)-furo[3,4-c]pyridin-2'-one, N-oxide;

spiro[1-(2,2-dimethyl)indanyl]-1,3'(1H̲)-furo[3,4-c]pyridin-2-(2-methyl-2-fluoropropyl)imine; and spiro[1-(2,2-dimethyl-1,2,3,4-tetrahydronaphthyl)]-1,3'(1'H̲)-furo[3,4-c]pyridin-2'-(2-methyl-2-fluoropropyl)imine.

Further, the compounds of formula (I) comprise the pyrrolo[3,4-c]pyridin-1(3H)-one derivatives having the formula (I-c)

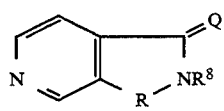 (I-c)

wherein Q, R and R⁸ are as defined under formula (I).

Preferred compounds represented by formula (I-c) are:

spiro[1-(2,2-dimethyl)indanyl]-1,3'(1'H̲)pyrrolo[3,4-c]pyridin-2'-one and spiro[1-(2,2-dimethyl)indanyl]-1,3'(1H̲)-pyrrolo[3,4-c]pyridin-1'-methyl-2'-one.

The compounds of formula (I) can be prepared from 4-(4',4'-dimethyloxazolin-2'-yl)pyridine of the formula

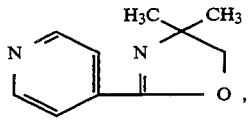

which is known from J. Org. Chem. 47 (13), 2633 (1982). Said starting compound is treated with LiCH₃ in a reaction-inert organic solvent at a temperature as low as −78° C. and the reaction mixture is allowed to warm up to about 0° C. After cooling again to about −78° C., the keto form of a radical R as described hereinabove is added. Said keto compounds have the formula

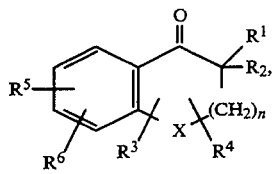

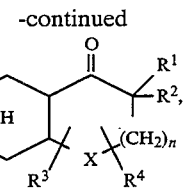

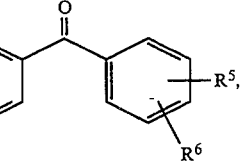

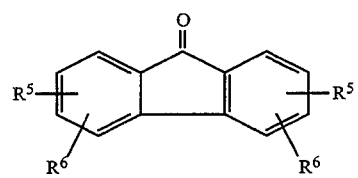

or

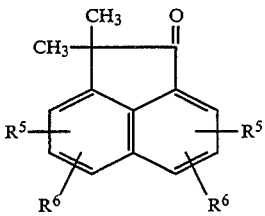

wherein n, R¹ to R⁶ and X are as defined under formula (I). The thus formed tertiary carbinol intermediate, which is not isolated, rearranges to a spiro-iminolactone of formula (I-d)

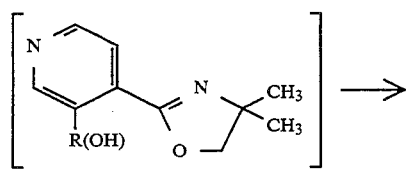

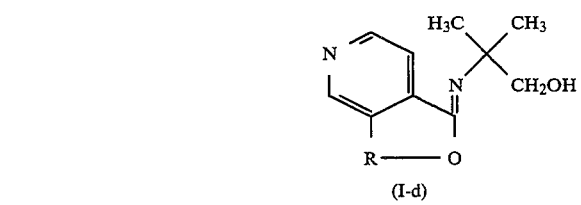

(I-d)

wherein R is as defined under formula (I). An example of such a compound is, e.g. spiro[1-(2,2-dimethyl)indan]-1,3'(1'H̲)furo[3,4-c]pyridin-2'-(1,1-dimethyl-2-hydroxyethyl)imine, the synthesis of which is described in Example 1. Reactions of this type are described in, e.g. J. Org. Chem. 47(13), 2633 (1982) and Tetrahedron 3,337 (1978). Surprisingly, the compound of formula (I-d) wherein R represents spiro[1,2,3,4-tetrahydronaphthyl)], said compound being represented by formula (I-d-1) further rearranges to the amide of formula (I-d-2).

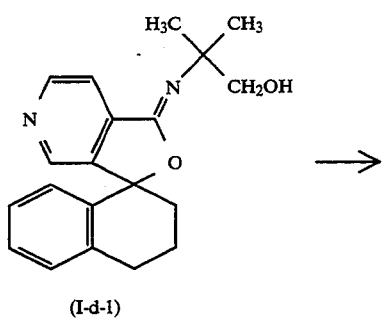

(I-d-1)

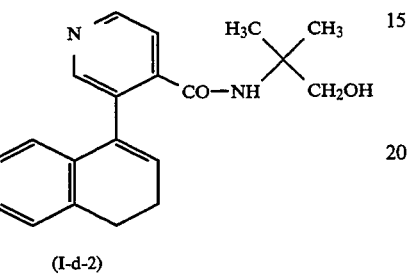

(I-d-2)

Alternatively, the compounds of formula (I) can also be prepared from N, N-diisopropyl pyridin-4-carboxamide of the formula

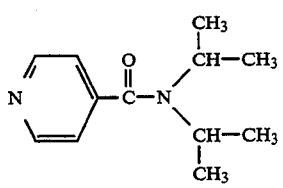

which is known from Tetr. Lett. 21, 4739 (1980).
Said starting compound is treated with lithium N-(1-methylethyl)2-propanamide (prepared from butyl lithium and N-(1-methylethyl)-2-propanamine) in a reaction-inert organic solvent at a temperature as low as $-78°$ C. and subsequently the keto form of a radical R as described hereinabove is added. Thus, a compound of formula (I-e) is formed wherein R(OH) represents R with R' being hydroxy

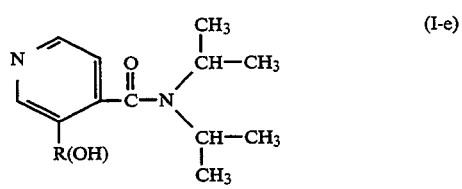

(I-e)

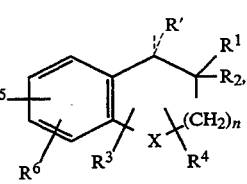

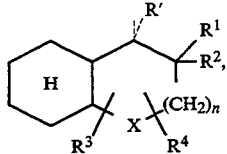

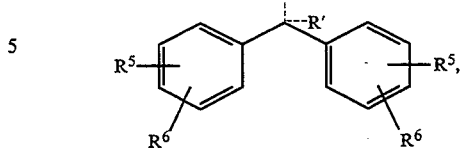

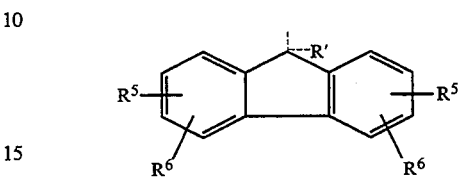

or

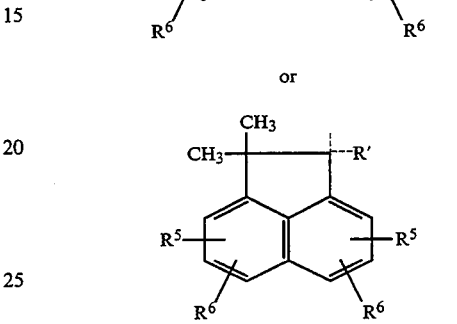

The isonicotinic acid derivatives of formula (I-a) wherein L is 1,1-dimethyl-2-hydroxyethylaminocarbonyl, said compound being represented by formula (I-f), can be prepared by catalytically hydrogenolyzing an iminolactone compound of formula (I-d) in a reaction-inert solvent.

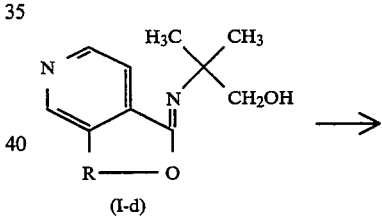

(I-d)

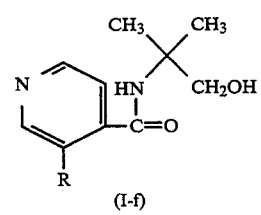

(I-f)

These compounds of formula (I-f) can be converted in an acid aqueous environment at an elevated temperature into the isonicotinic acid derivative of formula (I-g)

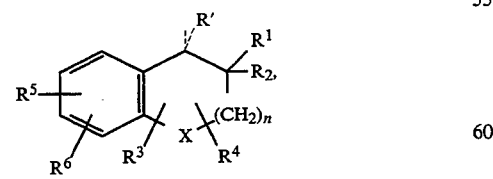

(I-g)

which can further be esterified following art-known procedures with an alcohol of formula $HOR^{9-a}$ (II), wherein $R^{9-a}$ is defined as $R^9$ but other than hydrogen, to an ester of formula (I-h).

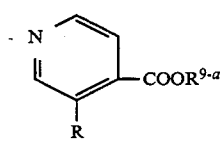

The carboxylic acids of formula (I-g) can also be prepared from the corresponding spiro-lactone of formula (I-b-1) by catalytic hydrogenolysis in a reaction-inert solvent.

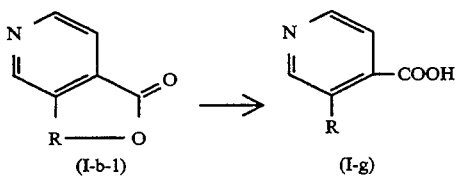

Furo[3,4-c]pyridin-1(3H)-one and -thione compounds of formula (I-b-1) can be obtained by reacting an iminolactone compound of formula (I-d) in an acid aqueous environment at an elevated temperature following art-known procedures.

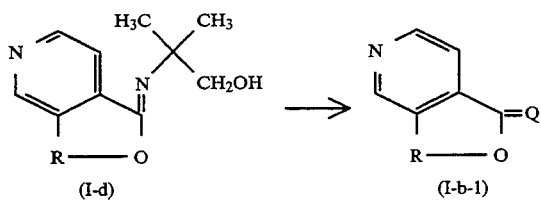

In some instances, the (thio)lactone of formula (I-b-1) may further rearrange to a (thio)carboxylic acid derivative wherein R' and $R^1$ form an extra bond.

Interestingly, treatment of an iminolactone compound of formula (I-d) in a concentrated acid, e.g. concentrated hydrochloric acid results in the formation of a lactam of formula (I-c-1).

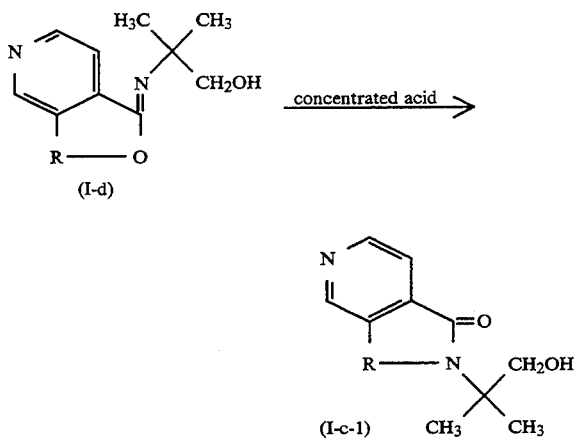

The compounds of formula (I-b-1) can also be obtained by reacting a compound of formula (I-e) wherein R(OH) is as defined hereinabove, in an acid aqueous environment at an elevated temperature following art-known procedures.

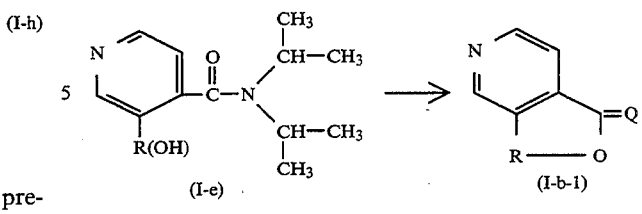

The spiro-lactam and spiro-thiolactam compounds of formula (I-c) can be prepared by reacting spiro-lactone and spiro-thiolactone compounds of formula (I-b), with ammonia or an amine of the formula $NH_2-R^8$, wherein $R^8$ is as defined under formula (I) at a temperature between 250° C. and 300° C., according to a method described in J. Am. Chem. Soc. 71, 896 (1949). The said reaction is preferably conducted in a closed reaction vessel, e.g. in a sealed thick-walled glass tube, in the presence of an excess of the amine compound. In some instances the desired spiro-lactam and spiro-thiolactam compounds of formula (I-c) are accompanied by (thio)amides of formula (I-a-1), which can be separated from one another following art-known purification procedures.

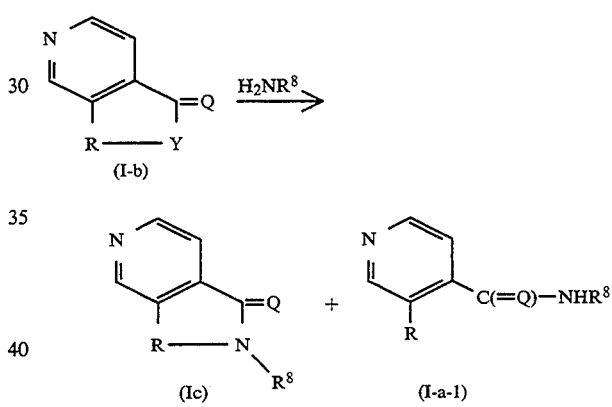

The spiro-thiolactone or the spiro-thiolactam compounds of formula (I-c) wherein Q is S, and the thioamides wherein L represents $C(=S)NR^{10}R^{11}$ can be obtained by reacting the corresponding compound wherein Q is O or L represents $C(=O)NR^{10}R^{11}$, with Lawesson's reagent in methylbenzene at an elevated temperature, preferably under reflux conditions.

The preparation of the iminolactone compounds of formula (I-d) is very particular, since the addition of the methyl lithium to the 4-(4', 4'-dimethyloxazolin-2'-yl)pyridine at a temperature of −78° C. has to be done in a completely waterfree solvent and with the exclusion of any moisture. Reaction-inert solvents are here e.g. dry ethers, which dissolve methyl lithium but do not react with it, for example, diethyl ether, dipropyl ethyl, 2,2'-oxybispropane, dioxane or tetrahydrofuran. In order to reach the required reaction temperature for addition of $CH_3Li$, the reaction mixture can be cooled in a $CO_2$ (dry ice)/2-propanone bath.

The catalytic hydrogenolysis of the compounds of formula (I-d) or (I-b-1) is performed by hydrogenation using native hydrogen. The latter is preferably prepared in a reaction-inert solvent, in the presence of a catalyst, by introduction of hydrogen. Said hydrogenolysis reaction is performed in a reaction-inert solvent such as, for example an alcohol or an ether, e.g. methanol, ethanol, isopropanol, dimethyl ether, 2,2'-oxybispropane, dioxane or tetrahydrofuran. The said catalyst is, for example, palladium-on-charcoal or platinum-on-charcoal.

Both the reaction of the iminolactone compounds of formula (I-d) to furo[3,4-c]-pyridine-1(3H)one compounds of formula (I-b) and the reaction of the 1,1-dimethyl-2-hydroxyethylisonicotinic acid amide compounds of formula (I-f) to the corresponding isonicotinic acid derivatives of formula (I-g) are saponifications known in the art. The said saponification reactions are conducted in the presence of a strong 4-6N mineral acid, at an elevated temperature. Examples of suitable mineral acids are hydrochloric acid, hydrobromic acid, sulfuric acid and the like. In order to reach the required elevated temperature, it is sufficient e.g. to boil the reaction mixture, preferably under reflux conditions.

The compounds of formula (I-b) (Q=NR$^7$) with fluorine in the iminoalkyl part can be prepared from the corresponding iminolactone alcohol of formula (I-d). The iminolactone alcohol is dissolved in a reaction-inert organic solvent, preferably a chlorohydrocarbon, and then mixed with an equimolar quantity of diethylaminosulfurtrifluoride (DAST). When the slightly exothermic reaction has ceased, stirring is continued for a few more hours and the fluorinated reaction product can be isolated from the reaction mixture by procedures known in the art. Similarly, the hydroxy group in the compounds of formula (I-e) can be converted into fluorine following the above described procedure, thus yielding a compound of (I-i) wherein R' is fluoro and the radical R may be represented as R(F) and L represents -CO-N(iPr)$_2$.

The esterification of the nicotinic acid derivatives of formula (I-g) to the ester of formula (I-h) can be conducted by procedures known in the art, e.g. by boiling the acid with an excess of the required alkanol of formula (II) in the presence of an acid, e.g. concentrated hydrochloric or sulfuric acid; or by converting the nicotinic acid derivative of formula (I-g) into an acyl halide, e.g. the acyl chloride, followed by reaction of the latter with the alkanol of formula (II).

The N-oxide forms of the compounds of formula (I) can conveniently be prepared by N-oxidation with an appropriate organic or inorganic peroxide such as, for example, hydrogen peroxide, perbenzoic acid, 3-chloroperbenzoic acid, t.butyl hydroperoxide and the like. Suitable solvents for said N-oxidation reactions are, for example, water, alkanols, e.g. methanol, ethanol and the like, halogenated hydrocarbons, e.g. dichloromethane, trichloromethane and the like.

The compounds of formula (I) are stable compounds and no precautionary measures are required for handling them.

The selective herbicidal action of the compounds according to the present invention is observed both when used pre- and postemergence of the weeds. Therefore, these compounds can be applied successfully for both preventive an curative selective control of weeds in crops of useful plants. The compounds of formula (I), however, are preferably used preventively.

The invention also relates to herbicidal compositions containing one or more inert carriers and, if desired, other adjuvants and as active ingredient a herbicidally effective amount of a compound of formula (I) as defined hereinabove. Further the invention relates to methods of controlling weeds by the application of the novel compounds to said weeds or to the locus thereof.

In the method for controling weeds according to the invention the compounds of formula (I) are used in unmodified form or, preferably, together with the adjuvants conventionally employed in the art of formulation. They are therefore formulated following art-known procedures to emulsifiable concentrates, directly sprayable or dilutable solutions, dilute emulsions, wettable powders, soluble powders, dusts, granulates, and also encapsulations in e.g. polymer substances. Depending on the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula (I) and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are aromatic hydrocarbons, preferably the fractions containing 8 to 12 carbon atoms, such as, alkylbenzene mixtures, e.g. dimethylbenzene mixtures or alkylated naphthalenes, aliphatic or alicyclic hydrocarbons such as paraffins, cyclohexane or tetrahydronaphtalene, alcohols such as ethanol, propanol or butanol, glycols and their ethers and esters, such as propylene glycol or dipropylene glycol ether, ketones such as cyclohexanone, isophorone or diacetone alcohol, strongly polar solvents such as N-methyl-2-pyrrolidone, dimethylsulfoxide or water, vegetable oils and their esters, such as rape, castor or soybean oil, possibly also silicon oil.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula (I) to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, earth alkaline metal salts or unsubstitued or ammonium salts and contain a $C_8$–$C_{22}$ alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (alifatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$ alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981, M. and J. Ash, "Encyclopedia of Surfactants", Vol. I-III, Chemical Publishing Co., New York, 1980-81.

The herbicidal compositions which are preferably employed in the method of the invention usually contain 0.1 to 99%, preferably 0.1 to 95% of a compound of formula (I), 1 to 99% of a solid or liquid adjuvant, and 0 to 25% preferably 0.1 to 25% of a surfactant. The commercial forms of said herbicidal compositions are advantageously concentrates which can easily be diluted by the end user.

The compositions can also contain further additives, such as, stabilizers, e.g. optionally epoxidized vegetable oils (epoxidized coconut, rape or soybean oil), defoamers, e.g. silicon oil, conservatives, viscosity regulators, binding materials, fillers and dung or other materials for special purposes.

Preferred formulations are composed in particular of the following constituents (%=percentage by weight):

| Emulsifiable concentrates | |
|---|---|
| active ingredient | 1 to 9%, preferably 2 to 5% |
| surfactant | 5 to 30% preferably 10 to 20% |
| liquid carrier | 5 to 94% preferably 70 to 85% |
| Dusts | |
| active ingredient | 0.1 to 10%, preferably 0.1 to 1% |
| solid carrier | 99.9 to 90%, preferably 99.9 to 99% |
| Suspension concentrates | |
| active ingredient | 5 to 75%, preferably 10 to 50% |
| water | 94 to 24%, preferably 88 to 30% |
| surfactant | 1 to 40%, preferably 2 to 30% |
| Wettable powders | |
| active ingredient | 0.5 to 90%, preferably 1 to 80% |
| surfactant | 0.5 to 20%, preferably 1 to 15% |
| solid carrier | 5 to 95%, preferably 15 to 90% |
| Granulates | |
| active ingredient | 0.5 to 30%, preferably 3 to 15% |
| solid carrier | 99.5 to 70%, preferably 97 to 85% |

The following examples are intended to illustrate and not to limit the scope of the present invention.

EXPERIMENTAL PART

Example 1: Preparation of:

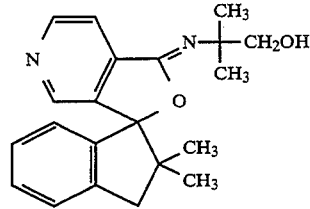

10.56 g of 2'-(4-pyridyl)-4', 4'-dimethyloxazoline (prepared as described in J. Org. Chem. 47(13), 2633, 1982) and 120 ml of tetrahydrofuran (dried over a molecular sieve) were cooled to −78° C. in an $CO_2$/acetone bath. 50 g of methyl lithium (1.6N in diethyl ether) were brought in a drop funnel by means of a syringe. The methyl lithium was added to the tetrahydrofuran solution over a few minutes, which caused the reaction solution to become orange. The solution was stirred for 1 hour at −78° C. and then warmed to 0° C. in an ice-/salt bath. The reaction solution became dark brown. The solution was stirred for 1 hour at 0° C. and cooled again to −78° C. A solution of 28.8 g of 2,2-dimethylindanone in 10 ml of tetrahydrofuran was added dropwise over 5 minutes. After stirring for 15 minutes at −75° C., the solution was warmed to room temperature in a water bath and was then poured in an aqueous saturated ammonium chloride solution. The water phase was extracted with ether and the combined organic layers were washed with brine, dried over $Na_2SO_4$ and evaporated, yielding 44.1 g of dark brown product. The latter was purified by column chromatography (silica gel;

CH3COOC2H5), yielding 7.06 g (35%) of the iminolactone (comp. 1.001). The ¹H and ¹³C NMR results and those of elementary analysis confirmed the expected iminolactone alcohol structure.

Example 2: Preparation of:

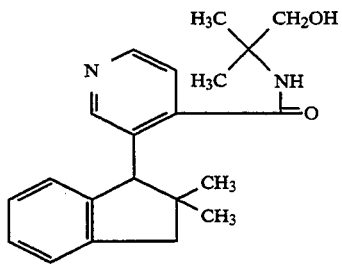

5.50 g of the iminolactone compound (comp. 1.001) was hydrogenated in 150 ml of methanol at room temperature and normal pressure in the presence of palladium-on-charcoal catalyst 5%. The catalyst was filtered off over diatomaceous earth and the filtrate was evaporated, yielding 5.60 g of red crystals. These were recrystallized from a mixture of methanol and ether, yielding 3.40 g (63%) of white crystals of N-(2-hydroxy-2,2-dimethylethyl)-3-(2,3-dihydro-2,2-dimethyl-1-H-inden-1-yl)-4-pyridinecarboxamide (comp. 3.024), mp. 112°—116° C.

Example 3: Preparation of:

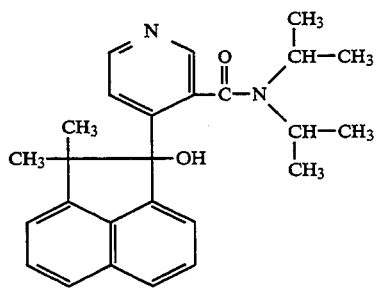

To a cooled (−80° C.) and stirred solution of 5.25 g of N-(1-methylethyl)-2-propanamine in 500 ml of dry tetrahydrofuran there were added 20 ml of butyl lithium (2.5M in hexane) and, after stirring for 1 hour at −80° C., 10.3 g of N,N-bis(1-methylethyl)-4-pyridinecarboxamide (prepared as described in Tetr. Lett. 21, 4739, 1980). Stirring at −80° C. was continued for 3 hours and then there were added 9.3 g of 2,2-dimethylacenaphthylen-1(2H)-one. The whole was stirred for 18 hours at room temperature and was then poured into water. The product was extracted with ether and the extract was dried, filtered and evaporated. The residue was purified by column chromatography (silica gel; CH2Cl2/CH3OH 95:5). The eluent of the desired fraction was evaporated, yielding 4.2 g (20.9% ) of (±)-3-(1,2-dihydro-1-hydroxy-2,2-dimethyl-1-acenaphthylenyl)-N,N-bis(1-methylethyl)-4-pyridinecarboxamide (comp. 5.006)

Example 4: Preparation of:

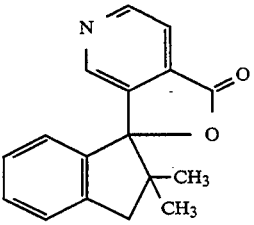

3.20 g of the iminolactone compound (comp. 1.001) were dissolved in 14.3 ml hydrochloric acid 4.5N. After stirring for 18 hours at reflux temperature, the reaction mixture was filtered and the clear, brown filtrate was brought to pH 4 with a sodium carbonate solution. The water phase was extracted with ether. The organic phase was washed with water and brine, dried over Na2SO4 and evaporated to 2.37 g (95%) of a brown oil, which crystallized upon standing, yielding 2′, 3′-dihydro-2′, 2-dimethylspiro[furo[3,4c]pyridin-3(1H), 1′[1H]-inden]-1-one; mp. 84° C. (comp. 4.001).

Example 5: Preparation of:

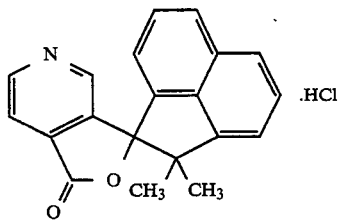

A mixture of 4.2 g of compound (5.006) and 100 ml of hydrochloric acid 2N was stirred for 12 hours at reflux temperature. After cooling, the reaction mixture was neutralized with a sodium carbonate solution. The product was extracted with ether and the extract was dried, filtered and evaporated. The residue was converted into the hydrochloride salt in ether by addition of 2-propanol saturated with HCl. The salt was filtered off, dried and purified by column chromatography (HPLC; silica gel; CH2Cl2/CH3OH 95:5). The eluent of the desired fraction was evaporated, yielding 0.4 g (11%) of 2,2-dimethyl-spiro-[acenaphthylene-1(2H),3′(1′H)-furo[3,4-c]pyridin]-1′-one hydrochloride; mp. 157.2° C. (comp. 4.018).

Example 6: Preparation of:

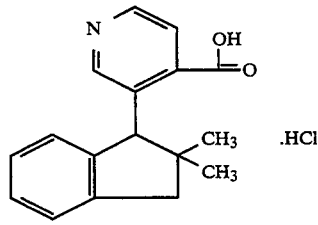

2.90 g of compound (3.024) were dissolved in 100 ml hydrochloric acid 6N and stirred for 14 hours at reflux temperature. A clear solution was formed which was evaporated to yield violet crystals. These were stirred in ether, filtered off, washed with ether and dried, yielding 3.2 g of 3-(2,3-dihydro-2,2-dimethyl-1H-inden-1-yl)-4-pyridinecarboxylic acid monohydrochloride; mp.

160°–164° C. According to gas chromatography the product is contained with 19% of 2-amino-2-methyl-1-propanol.

Example 7: Preparation of:

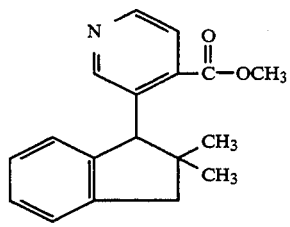

3.18 g of compound (3.027) were dissolved in 160 ml of methanol. 6.4 ml of concentrated sulfuric acid was added dropwise and the solution was refluxed for 3 days, yielding a dark brown, clear solution. The latter was evaporated and the residual oil was neutralized with an aqueous sodium carbonate solution. The product was extracted with dichloromethane and the extract was washed with a diluted sodium carbonate solution and brine, dried over Na₂SO₄ and evaporated, yielding 2.80 g of a dark brown oil. The oil was filtered over silica gel, yielding 2.00 g (83.6%) of methyl 3-(2,3-dihydro-2,2-dimethyl-1H-inden-1-yl)-4-pyridinecarboxylate (comp. 3.001).

Example 8: Preparation of:

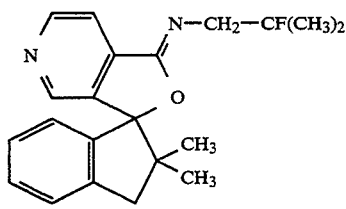

3.70 g of compound (1.001) were dissolved in 30 ml of dichloromethane. 1.77 g of diethylaminosulfur trifluoride (DAST) were added dropwise over 5 minutes at room temperature while stirring (slightly exothermic reaction). The reaction mixture was stirred for 18 hours at room temperature. The brown reaction solution was cooled to 0° C. and mixed with 60 ml of ice-water. The product was extracted with dichloromethane. The organic phase was washed with water and NaHCO₃ (sat.), dried over Na₂CO₃ and evaporated. The residue was purified by column chromatography (silica gel; CH₃COOC₂H₅). The eluent of the desired fraction was evaporated, yielding 2.29 g (66.3%) of yellowish crystals of N-(2',3'-dihydro-2',2'-dimethylspiro[furo[3,4-c]pyridin-3(1H), 1'[1 H]-inden]-1-ylidene)-2-fluoro-2-methylpropanamine; mp. 90°–92° C. (comp. 2.001).

Example 9: Preparation of:

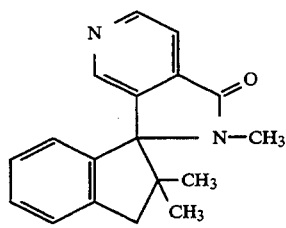

2.66 g compound (4.001) and 2 g of methanamine were heated for 5 hours at 280° C. in a sealed thick-walled glass tube. After cooling, the reaction mixture was poured into 100 ml of dichloromethane and the whole was washed with water, dried over Na₂SO₄ and evaporated. The residue was purified by column chromatography (silica gel; CH₃COOC₂H₅). The eluent of the desired fraction was evaporated, yielding 0.70 g of a viscous oil, being 2,3-dihydro-2,2,2'-trimethylspiro[1H-indene-1,3'[3 H]pyrrolo[3,4-c]pyridin]-1'(2'H)-one) (comp. 4.019).

Another fraction yielded the reduced 3-(2,3-dihydro-2,2-dimethyl-1H-inden-1-yl)-Nmethyl-4-pyridinecarboxamide, mp. 146°–148° C. (comp. 3.002), of formula

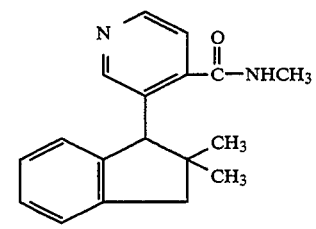

The ratio of title product to the reduced 4-pyridinecarboxamide is 1 to 4.

Example 10: Preparation of:

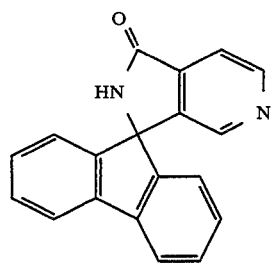

A mixture of 4 g of compound (4.016) in 100 ml of ammonium hydroxide was stirred in a sealed thick-walled glass tube at 240° C. or 18 hours. After cooling, the reaction mixture was poured into water. The product was extracted with dichloromethane and the extract was dried over Na₂SO₄ and evaporated. The residue was recrystallized from diisopropylether and dried, yielding 2.7 g (67%) of spiro[9H-fluorene-9,3'[3 H]pyrrolo[3,4-c]pyridin]-1'(2'H)-one; mp. 208.5° C (comp. 4.028).

Example 11: Preparation of:

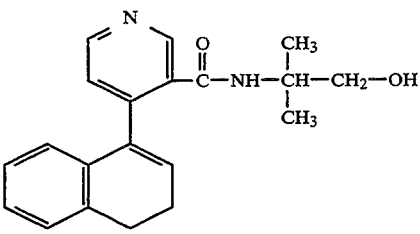

To a stirred and cooled (−78° C.) solution of 26.4 g of 4-(4,5-dihydro-4,4-dimethyl-2-oxazolyl)pyridine in 200 ml of tetrahydrofuran (distilled over LiAlH₄) there were added 70 ml of methyl lithium under a nitrogen atmosphere. Stirring was continued for 2 hours at 0° C.

At −78° C., there was added a solution of 22 g of 3,4-dihydro-1(2H)naphthalenone in 50 ml of tetrahydrofuran. After stirring overnight at room temperature, the reaction mixture was poured into a saturated NH₄Cl solution. The product was extracted with diethyl ether and the extract was dried, filtered and evaporated. The residue was recrystallized from acetonitrile, yielding 8.5 g (17.6%) of 3-(3,4-dihydro-1-naphthalenyl)-N-(2-hydroxy-1,1-dimethylethyl)-4-pyridinecarboxamide; mp. 156.8° C. (comp. 3.031).

Example 12: Preparation of:

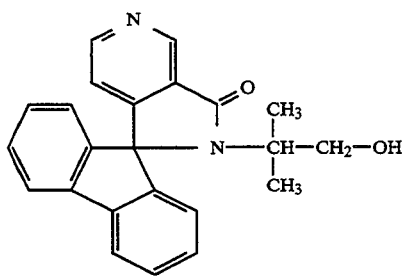

A mixture of 5 g of compound (1.017) and 25 ml of concentrated hydrochloric acid was refluxed for 48 hours. The reaction mixture was purified by column chromatography (silica gel; CH₂Cl₂/CH₃OH 95:5). The eluent of the desired fraction was evaporated and the residue was recrystallized from acetonitrile, yielding 0.7 g (14%) of 2'-(2hydroxy-1,1-dimethylethyl)spiro[9H-fluorene-9,3'[3H]pyrrolo[3,4-c]pyridin]-1'(2'H)one; mp. 194.9° C. (comp. 4.030).

Example 13: Preparation of:

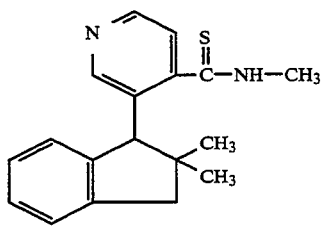

A mixture of 2.0 g of compound (3.002), 3.5 g of Lawesson's reagent and some methylbenzene were stirred and heated for 1 hour. After cooling, the reaction mixture was partitioned between dichloromethane and NaHCO₃ (1M). The organic layer was separated, dried, filtered and evaporated. The residue was purified by column chromatography (silica gel; CH₃COOC₂H₅). The eluent of the desired fraction was evaporated, yielding 1.8 g (85%) of N-methyl-3-(2,3-dihydro-2,2-dimethyl-1H-inden-1-yl)-4-pyridine thiocarboxamide; mp. 187°–189° C. (comp. 3.029).

Example 14: Preparation of:

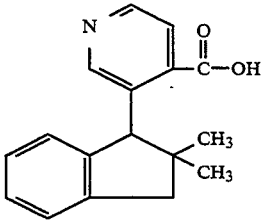

A mixture of 53 g of compound (4.001) and 500 ml of tetrahydrofuran was hydrogenated at normal pressure and room temperature in the presence of 10 g of palladium-on-charcoal catalyst 5%. After the calculated amount of hydrogen was taken up, the catalyst was filtered off and washed with tetrahydrofuran. The combined filtrates were evaporated, yielding 51.6 g (97%) of 3-(2,3-dihydro-2,2-dimethyl-1H-inden-1-yl)-4-pyridinecarboxylic acid; mp. 254°–257° C. (comp. 3.027).

Example 15: Preparation of:

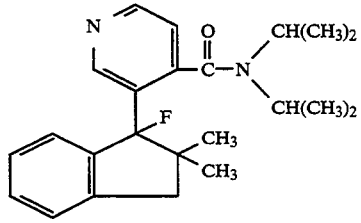

To a solution of 3.66 g of compound (5.001) in 30 ml of dichloromethane there were added 1.61 g of diethylaminosulfur trifluoride and the whole was refluxed overnight. The reaction mixture was washed with water, dried, filtered and evaporated, yielding 2.4 g (65%) of N,N-bis(1-methylethyl)-3-(2,3-dihydro-2,2-dimethyl-1-fluoro-1H-inden-1-yl)-4-pyridinecarboxamide (amorphous) (comp. 5.007).

Example 16: Preparation of:

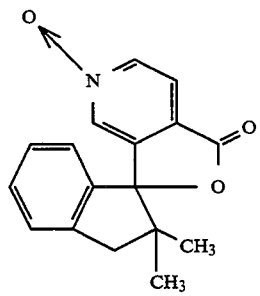

To a cooled (0° C.) solution of 1.0 g of compound (4.001) in 6 ml of dichloromethane there was added dropwise a solution of 0.72 g of 3-chloroperbenzoic acid in 6 ml of dichloromethane. After stirring for 22 hours at room temperature, the reaction mixture was filtered through 40 g of basic alox (Al₂O₃) and the filtrate was evaporated, yielding 0.8 g (75%) of 2',3'-dihydro-2',2-dimethyl-spiro[furo[3,4-c]pyridin-3(1H), 1'[1 H]inden]-1-one, N-oxide; mp. 150°–153° C. (comp. 4.031).

Example 17: Preparation of:

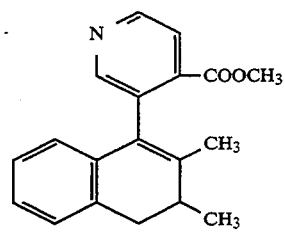

A solution of 2.9 g of compound (1.010) in hydrochloric acid (4.5N) was refluxed overnight. The reaction mixture was basified to pH 8 with conc. Na$_2$CO$_3$ solution. The product was extracted with dichloromethane in a Kutscher-Steudel apparatus and the extract was dried, filtered and evaporated. The residue was filtered over silica gel, yielding 3-(3,4-dihydro-2,3-dimethyl-1-naphthyl)-4-pyridinecarboxylic acid. The latter was esterified with methanol in the presence of sulfuric acid, yielding methyl 3-(3,4-dihydro-2,3-dimethyl-1-naphthyl)-4-pyridinecarboxylate as an oil (comp. 3.009).

Example 18: Separation into the pure enantiomers of:

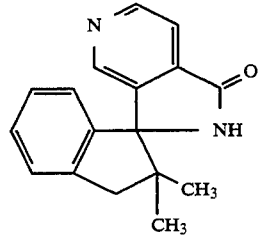

0.164 g of compound (4.020) (prepared following the procedure described in example 10) were separated into the pure enantiomers by preparative column chromatography (Chiralcell OD ®; hexane/C$_2$H$_5$OH 85:15). The eluent of the separated fractions was evaporated, yielding resp. 0.050 g (30.5%) of A enantiomer; mp. 233.8° C. (e.e.=97%) (comp. 4.032) and 0.050 g (30.5%) of B enantiomer; mp. 223.5° C. (e.e.=96%) (comp. 4.033).

All compounds listed in tables 1–5 were prepared following methods of preparation described in examples 1–18, as is indicated in the column Ex. No.

TABLE 1

| Co. No. | Ex. No. | R | Physical data |
|---|---|---|---|
| 1.001 | 1 | indanyl-CH$_3$,CH$_3$ | colourless resin |
| 1.002 | 1 | indanyl-CH$_3$ | viscous oil |
| 1.003 | 1 | tetralinyl-CH$_3$,CH$_3$ | amorphous crystals |
| 1.004 | 1 | tetralinyl-CH$_3$ | mp. 147–152° C. |
| 1.005 | 1 | benzocycloheptyl | — |
| 1.006 | 1 | phenyl-CH$_3$-O | — |
| 1.007 | 1 | phenyl-CH$_3$,CH$_3$-O | — |
| 1.008 | 1 | chromanyl-CH$_3$,CH$_3$ | — |
| 1.009 | 1 | chromanyl-CH$_3$,CH$_3$ | — |
| 1.010 | 1 | tetralinyl-CH$_3$,CH$_3$ | viscous oil |
| 1.011 | 1 | decahydronaphthyl | — |

TABLE 1-continued

[Structure: pyridine-C(=N-C(CH3)2-CH2OH)-O-R]

| Co. No. | Ex. No. | R | Physical data |
|---|---|---|---|
| 1.012 | 1 | (octahydroindene with gem-dimethyl and CH3) | — |
| 1.013 | 1 | (octahydroindene with gem-dimethyl and 2,2-diCH3) | — |
| 1.014 | 1 | (decahydronaphthalene with methyl) | — |
| 1.015 | 1 | (decahydronaphthalene with gem-dimethyl and CH3) | — |
| 1.016 | 1 | (decahydronaphthalene with gem-dimethyl and 2,2-diCH3) | — |
| 1.017 | 1 | (fluorenyl with methyl) | — |
| 1.018 | 1 | (diphenylmethyl with methyl) | — |
| 1.019 | 1 | (acenaphthylene with gem-dimethyl groups) | — |
| 1.020 | 1 | (benzocycloheptene with gem-dimethyl and 2,2-diCH3) | — |

TABLE 2

[Structure: pyridine-C(=N-CH2-CF(CH3)2)-O-R]

| Co. No. | Ex. No. | R | Physical data |
|---|---|---|---|
| 2.001 | 8 | (indane with gem-dimethyl and 2,2-diCH3) | mp. 93–95° C. |
| 2.002 | 8 | (tetrahydronaphthalene with gem-dimethyl and 2,2-diCH3) | mp. 123–126° C. |
| 2.003 | 8 | (tetrahydronaphthalene with gem-dimethyl and CH3) | amorphous crystals |

TABLE 3

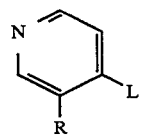

| Co. No. | Ex. No. | R | L | Physical data |
|---|---|---|---|---|
| 3.001 | 7 | (indane with methyl and 2,2-diCH3) | COOCH3 | oil |

TABLE 3-continued

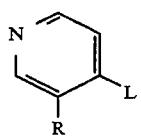

| Co. No. | Ex. No. | R | L | Physical data |
|---|---|---|---|---|
| 3.002 | 9 | (2,2-dimethylindan-1-yl) | CONHCH$_3$ | mp. 146–148° C. |
| 3.003 | 9 | (2,2-dimethylindan-1-yl) | CONH—C$_6$H$_5$ | mp. 172–176° C. |
| 3.004 | 7 | (2,2-dimethyl-1,2,3,4-tetrahydronaphthalen-1-yl) | COOCH$_3$ | oil |
| 3.005 | 7 | (indan-1-yl) | COOCH$_3$ | — |
| 3.006 | 7 | (1,2,3,4-tetrahydronaphthalen-1-yl) | COOCH$_3$ | — |
| 3.007 | 7 | (2-methyl-1,2,3,4-tetrahydronaphthalen-1-yl) | COOCH$_3$ | oil |
| 3.008 | 7 | (benzocycloheptan-5-yl) | COOCH$_3$ | — |
| 3.009 | 17 | (2,3-dimethyl-3,4-dihydronaphthalen-1-yl) | COOCH$_3$ | oil |
| 3.010 | 7 | (3-methyl-2,3-dihydrobenzofuran-3-yl) | COOCH$_3$ | — |
| 3.011 | 7 | (2,2-dimethyl-3-methyl-2,3-dihydrobenzofuran-3-yl) | COOCH$_3$ | HCl mp. 142.5° C. |

TABLE 3-continued

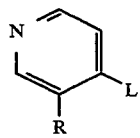

| Co. No. | Ex. No. | R | L | Physical data |
|---|---|---|---|---|
| 3.012 | 7 | (chroman-4-yl, 2,2-dimethyl) | COOCH$_3$ | — |
| 3.013 | 7 | (chroman-4-yl, 3,3-dimethyl) | COOCH$_3$ | — |
| 3.014 | 7 | (octahydro-1H-inden-1-yl) | COOCH$_3$ | — |
| 3.015 | 7 | (octahydro-1H-inden-1-yl, 2-methyl) | COOCH$_3$ | — |
| 3.016 | 7 | (octahydro-1H-inden-1-yl, 2,2-dimethyl) | COOCH$_3$ | — |
| 3.017 | 7 | (decahydronaphthalen-1-yl) | COOCH$_3$ | — |
| 3.018 | 7 | (decahydronaphthalen-1-yl, 2-methyl) | COOCH$_3$ | — |
| 3.019 | 7 | (decahydronaphthalen-1-yl, 2,2-dimethyl) | COOCH$_3$ | — |
| 3.020 | 7 | (fluoren-9-yl) | COOCH$_3$ | — |
| 3.021 | 7 | (diphenylmethyl) | COOCH$_3$ | HCl/mp. 139.9° C. |

TABLE 3-continued

[Structure: pyridine with R at 3-position and L at 4-position]

| Co. No. | Ex. No. | R | L | Physical data |
|---|---|---|---|---|
| 3.022 | 7 | 2,2-dimethyl-acenaphthylene group (CH₃, CH₃ on bridging carbon) | COOCH₃ | — |
| 3.023 | 7 | 2,3-dimethyl-tetrahydronaphthalen-1-yl | COOCH₃ | oil |
| 3.024 | 2 | 2,2-dimethyl-indan-1-yl | CONHC(CH₃)₂CH₂OH | mp. 110–116° C. |
| 3.025 | 2 | 2,2-dimethyl-tetrahydronaphthalen-1-yl | CONHC(CH₃)₂CH₂OH | amorphous |
| 3.026 | 2 | 2,3-dimethyl-tetrahydronaphthalen-1-yl | CONHC(CH₃)₂CH₂OH | — |
| 3.027 | 14 | 2,2-dimethyl-indan-1-yl | COOH | mp. 254–257° C. |
| 3.028 | 6 | (C₆H₅)₂—CH— | COOH | — |
| 3.029 | 13 | 2,2-dimethyl-indan-1-yl | C(=S)NHCH₃ | mp. 187–189° C. |
| 3.030 | 2 | (C₆H₅)₂—CH— | CONHC(CH₃)₂CH₂OH | mp. 159.5° C. |
| 3.031 | 11 | 3,4-dihydronaphthalen-1-yl | CONHC(CH₃)₂CH₂OH | mp. 156.8° C. |
| 3.032 | 14 | 2,2-dimethyl-2,3-dihydrobenzofuran-3-yl | COOH | mp. 245° C. |

TABLE 4

Structure: pyridine with N, substituted with C(=Q) group and R—Y group.

| Co. No. | Ex. No. | Q | Y | R | Physical Data |
|---|---|---|---|---|---|
| 4.001 | 4 | O | O | 2,2-dimethylindane | mp. 98.6° C. |
| 4.002 | 4 | O | O | 2,2-dimethyl-tetrahydronaphthalene | mp. 105–109° C. |
| 4.003 | 4 | O | O | 2-methyl-tetrahydronaphthalene | — |
| 4.004 | 4 | O | O | benzocycloheptane | — |
| 4.005 | 4 | O | O | 2-methyl-chroman-like (CH(CH₃)–O-phenyl) | — |
| 4.006 | 5 | O | O | 2,2-dimethyl-chroman-like (C(CH₃)₂–O-phenyl) | mp. 155.6° C. |
| 4.007 | 5 | O | O | 3,3-dimethylchroman | mp. 128–132° C. |
| 4.008 | 4 | O | O | dimethyl-benzocycloheptane | — |
| 4.009 | 4 | O | O | 2,2-dimethylchroman | — |
| 4.010 | 4 | O | O | octahydroindane | — |

TABLE 4-continued
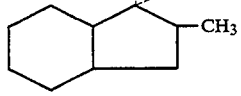
| Co. No. | Ex. No. | Q | Y | R | Physical Data |
|---|---|---|---|---|---|
| 4.011 | 4 | O | O | 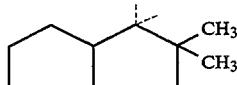 | — |
| 4.012 | 4 | O | O | 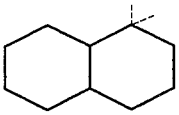 | — |
| 4.013 | 4 | O | O | 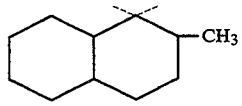 | — |
| 4.014 | 4 | O | O | 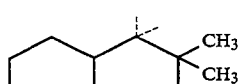 | — |
| 4.015 | 4 | O | O | 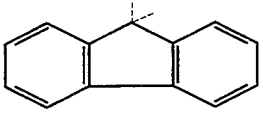 | — |
| 4.016 | 4 | O | O | 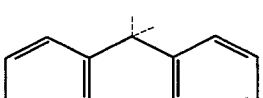 | mp. 202.1° C. |
| 4.017 | 4 | O | O | 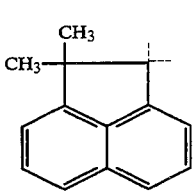 | mp. 134–135.2° C. |
| 4.018 | 5 | O | O | 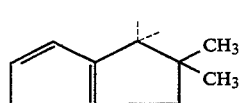 | mp. 157.2° C. |
| 4.019 | 9 | O | N—CH$_3$ | 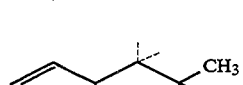 | oil |
| 4.020 | 10 | O | N—H |  | mp. 241° C. |

TABLE 4-continued
| Co. No. | Ex. No. | Q | Y | R | Physical Data |
|---|---|---|---|---|---|
| 4.021 | 10 | O | N—H | 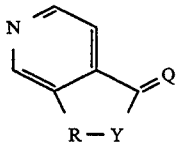 | — |
| 4.022 | 9 | O | N—C$_2$H$_5$ | 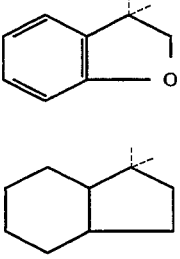 | — |
| 4.023 | 9 | O | N—CH(CH$_3$)$_2$ | 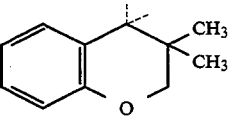 | — |
| 4.024 | 9 | O | N—C(CH$_3$)$_3$ | 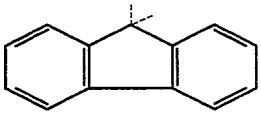 | — |
| 4.025 | 9 | O | N—C$_2$H$_5$ | 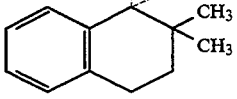 | — |
| 4.026 | 13 | S | O | 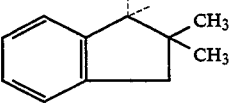 | mp. 112–114° C. |
| 4.027 | 13 | S | O | 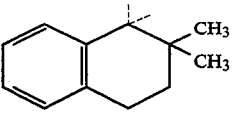 | — |
| 4.028 | 10 | O | N—H | 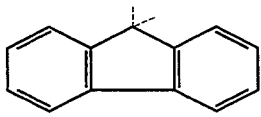 | mp. 208.5° C. |
| 4.029 | 10 | O | N—H | 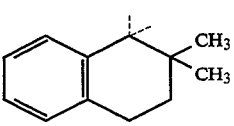 | — |
| 4.030 | 12 | O | N—C(CH$_3$)$_2$CH$_2$OH | 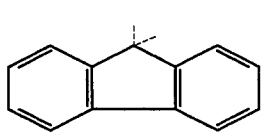 | mp. 194.9° C. |

TABLE 4-continued

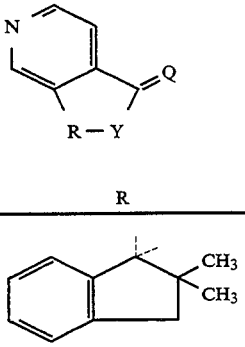

| Co. No. | Ex. No. | Q | Y | R | Physical Data |
|---|---|---|---|---|---|
| 4.031 | 16 | O | O | 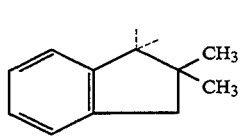 | N-oxide mp. 150–153° C. |
| 4.032 | 18 | O | NH | 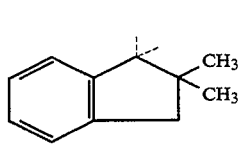 | A, mp. 233.8° C. (e.e. = 97%) |
| 4.033 | 18 | O | NH | 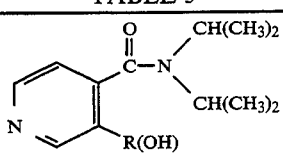 | B, mp. 233.5° C. (e.e. = 96%) |

TABLE 5

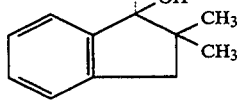

| Co. No. | Ex. No. | R(OH) | Physical data |
|---|---|---|---|
| 5.001 | 3 | 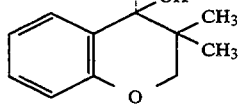 | mp. 210–213° C. |
| 5.002 | 3 | 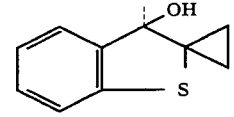 | mp. 232–234° C. |
| 5.003 | 3 | 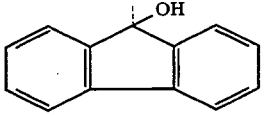 | mp. 232–236° C. |
| 5.004 | 3 | 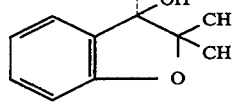 | mp. 192.8° C. |
| 5.005 | 3 | 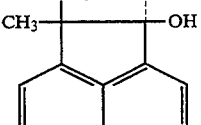 | mp. 250.5° C. |
| 5.006 | 3 | 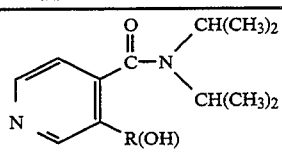 | — |
| 5.007 | 15 | 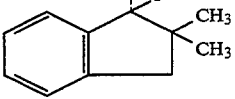 | amorphous |

COMPOSITION EXAMPLES

Example 19: Composition examples for liquid active ingredients of formula (I) (percentages are by weight)

| a) Emulsifiable concentrates | a) | b) | c) |
|---|---|---|---|
| compound of formula (I) | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| dimethylbenzene mixture | 70% | 25% | 20% |

Emulsions of any required concentration could be produced from such concentrate by dilution with water.

| b) Solutions | a) | b) | c) | d) |
|---|---|---|---|---|
| compound of formula (I) | 80% | 10% | 5% | 95% |
| propylene glycol monoethyl ether | 20% | — | — | — |
| polyethylene glycol (MG 400) | — | 70% | — | — |
| N-methyl-2-pyrrolidone | — | 20% | 5% | — |
| epoxidized coconut oil | — | — | 1% | 5% |
| petroleum distillate (boiling range 160–190° C.) | — | — | 89% | — |

These solutions were suitable for application in the form of microdrops.

| c) Granulates | a) | b) | c) | d) |
|---|---|---|---|---|
| compound of formula (I) | 5% | 10% | 8% | 21% |
| kaolin | 94% | — | — | 79% |
| highly dispersed silicic acid | 1% | — | 13% | 7% |
| attapulgite | — | 90% | — | 18% |

The active ingredient was dissolved in methylene chloride, the solution was sprayed onto the carrier, and the solvent was subsequently evaporated off in vacuo.

| d) Dusts | a) | b) |
|---|---|---|
| compound of formula (I) | 2% | 5% |
| highly dispersed silicic acid | 1% | 5% |
| talcum | 97% | — |
| kaolin | — | 90% |

Ready-for-use dusts were obtained by intimately mixing the carriers with the active ingredient.

Example 20: Composition examples for solid compounds of formula (I) (percentages are by weight)

| a) Wettable powders | a) | b) | c) |
|---|---|---|---|
| compound of formula (I) | 25% | 50% | 75% |
| sodium lignosulfonate | 5% | 5% | — |
| sodium laurylsulfate | 3% | — | 5% |
| sodium diisobutylnaphthalensulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient was thoroughly mixed with the adjuvants and the mixture was thoroughly ground in a suitable mill, affording wettable powders which could be diluted with water to give suspensions of the desired concentration.

| b) Emulsifiable concentrate | a) |
|---|---|
| compound of formula (I) | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| dimethylbenzene mixture | 50% |

Emulsions of any required concentration could be obtained from this concentrate by dilution with water.

| c) Dusts | a) | b) |
|---|---|---|
| compound of formula (I) | 5% | 8% |
| talcum | 95% | — |
| kaolin | — | 92% |

| d) Extruder granulate | a) |
|---|---|
| compound of formula (I) | 10% |
| sodium lignosulfate | 2% |
| carboxymethylcellulose | 1% |
| kaolin | 87% |

The active ingredient was mixed and ground with the adjuvants, and the mixture was subsequently moistened with water. The mixture was extruded and dried in a stream of air.

| e) Coated granulate | a) |
|---|---|
| compound of formula (I) | 3% |
| polyethylene glycol (mol. wt. 200) | 3% |
| kaolin | 94% |

The finely ground active ingredient was uniformly applied, in a mixer, to the kaolin moistened with polyethylene glycol. Non-dusty coated granulates were obtained in this manner.

| f) Suspension concentrate | a) |
|---|---|
| compound of formula (I) | 40% |
| ethylene glycol | 10% |
| nonylphenol polyethylene glycol ether (15 moles of ethylene oxide) | 6% |
| sodium lignosulfate | 10% |
| carboxymethylcellulose | 1% |
| 37% aqueous formaldehyde solution | 0.2% |
| silicone oil in the form of a 75% aqueous emulsion | 1% |
| water | 31.8% |

The finely ground active ingredient was intimately mixed with the adjuvants, giving a suspension concentrate from which suspension of any desired concentration could be obtained by dilution with water.

BIOLOGICAL EXAMPLES

Example 21: Preemergence herbicidal action

In a greenhouse, immediately after sowing the test plants in seed dishes, the surface of the soil was treated with an aqueous dispersion of the test compounds, obtained from a 25% emulsifiable concentrate.

Several concentration series of test compound per hectare were used. The seed dishes were kept in the greenhouse at 22°–25° C. and 50°–70% relative humidity and the test was evaluated 3 weeks later.

The herbicidal action is evaluated by means of a nine-step rating (1=total destruction of the test plants, 9=no herbicidal action on the test plants) in comparison with an untreated control group.

Degrees 1 to 4 (in particular from 1 to 3) point to a good to very good herbicidal action. Degrees 6 to 9 (in particular from 7 to 9) point to a high tolerance (in particular with cultivated plants).

The data obtained using the compounds 1.003 and 3.001 are summarized in Table 6.

TABLE 6

| Tested compound: | (1.003) | | | (3.001) | | |
|---|---|---|---|---|---|---|
| dosage (g/ha) | 1000 | 500 | 250 | 1000 | 500 | 250 |
| wheat | 8 | 9 | 9 | 6 | 6 | 7 |
| maize | 9 | 9 | 9 | 6 | 6 | 8 |
| millet | 7 | 9 | 9 | 7 | 9 | 9 |
| soy beans | 8 | 9 | 9 | 6 | 6 | 8 |
| sun flower | 9 | 9 | 9 | 6 | 8 | 9 |
| cotton | 9 | 9 | 9 | 6 | 6 | 7 |
| *Digitaria sang.* | 1 | 1 | 2 | 1 | 1 | 1 |
| *Echinochloa c. galli* | 1 | 4 | 4 | 1 | 4 | 4 |
| *Sida spinosa* | 2 | 4 | 4 | 2 | 3 | 3 |
| *Amaranthus retrofl.* | 2 | 2 | 3 | 1 | 2 | 2 |
| *Chenopodium album* | 2 | 2 | 2 | 2 | 2 | 2 |
| *Solanum nigrum* | 1 | 2 | 4 | 1 | 1 | 1 |
| *Viola tricolor* | 3 | 4 | 4 | 2 | 2 | 3 |
| *Veronica sp.* | 2 | 4 | 5 | 2 | 2 | 2 |

Example 22: Postemergence herbicidal action (contact herbicide)

A large number of plants, both monocotyle and dicotyle were sprayed postemergence (in the 4 to 6 leaf stage) with an aqueous active ingredient dispersion in rates of 1000 and 500 g of test compound per hectare and kept at 24°–26° C. and 45–60% relative humidity. The test was evaluated 15 days after treatment in accordance with the same rating as employed in the preemergence test. In this test, the compounds of formula (I) were also most effective against the tested weeds whereas the cultivated plants remained unaffected.

The data obtained using the compounds 1.003 and 3.001 are summerized in Table 7.

TABLE 7

| Tested compound: | (1.003) | | (3.001) | |
|---|---|---|---|---|
| dosage (g/ha) | 1000 | 500 | 1000 | 500 |
| barley | 7 | 8 | 7 | 9 |
| wheat | 6 | 7 | 6 | 7 |
| maize | 8 | 9 | 6 | 8 |
| millet | 8 | 9 | 6 | 9 |
| soy beans | 6 | 7 | 4 | 6 |
| sun flower | 7 | 9 | 6 | 6 |
| cotton | 6 | 6 | 6 | 7 |
| *Digitaria sang.* | 3 | 4 | 4 | 6 |
| Echinochloa | 4 | 5 | 4 | 5 |
| Abutilon | 4 | 5 | 3 | 4 |
| Xanthium sp. | 3 | 4 | 3 | 4 |
| *Amaranthus retrofl.* | 3 | 3 | 3 | 4 |
| *Chenopodium album* | 3 | 3 | 2 | 3 |
| *Solanum nigrum* | 2 | 2 | 2 | 2 |
| Ipomoea | 3 | 4 | 3 | 4 |
| Galium | 4 | 4 | 4 | 5 |
| *Viola tricolor* | 4 | 4 | 2 | 3 |
| *Veronica sp.* | 2 | 4 | 2 | 2 |

Example 23: Herbicidal action for rice and water rice (paddy)

The water weeds Echinochloa crus galli and Monochoria vag. Scirpus and Sagittaria were sown in a plastic container (60 cm² surface, 500 ml volume). The container is then filled with water up to the soil surface. After 3 days, the container was watered to such an extent that a water layer of 3–5 mm covered the surface. Then, an aqueous emulsion of the test substance was squirted on the crops. The applied dosage corresponded to an amount of active material of 0.5 to 4 kg a.i. per hectare (amount of solution corresponds to 550 l/ha). The plant container is then kept in the greenhouse optimum circumstances for growing the rice weeds: 25°–30° C. and high relative humidity. The evaluation of this test was made 3 weeks later. The tested compounds were found to damage the weeds but not the rice.

The data obtained using the compounds 1.003 and 3.001 are summarized in Table 8.

TABLE 8

| Tested compound: | (1.003) | | | | (3.001) | | | |
|---|---|---|---|---|---|---|---|---|
| dosage (g/ha) | 1000 | 500 | 250 | 125 | 1000 | 500 | 250 | 125 |
| rice | 5 | 6 | 6 | 6 | 5 | 6 | 7 | 7 |
| *Echinochloa c. galli* | 1 | 1 | 1 | 1 | 1 | 1 | 1 | 1 |
| Scirpus sp. | 1 | 1 | 1 | 4 | 2 | 2 | 2 | 3 |
| *Monochoria vag.* | 1 | 1 | 1 | 2 | 1 | 1 | 1 | 1 |
| Sagittaria sp. | 4 | 4 | 4 | 5 | 4 | 4 | 4 | 5 |

We claim:
1. A compound having the formula

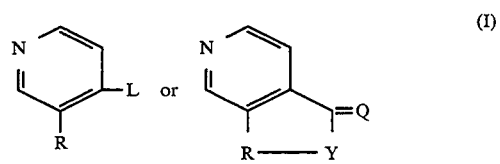
(I)

an acceptable addition salt, a stereochemically isomeric form or a N-oxide thereof, wherein R is attached to the pyridinyl group by a single bond or by a spiro-bond, and R has the formula

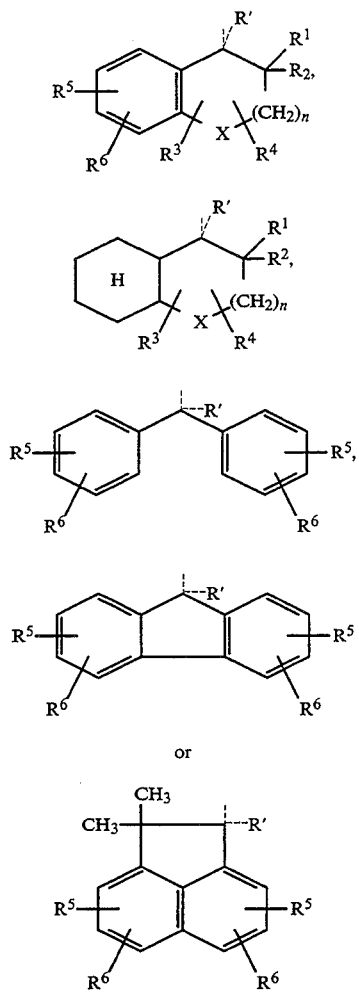

wherein

R' is hydrogen, fluoro, hydroxy or a spiro-bond;

$R^1$ and $R^2$ are each independently hydrogen, $C_{1-6}$alkyl or $R^1$ and $R^2$ together with the carbon atom to which they are connected form a spiro $C_{3-6}$cycloalkyl group; or R' and $R^1$ form an extra bond;

$R^3$ and $R^4$ are each independently hydrogen or $C_{1-6}$alkyl;

$R^5$ and $R^6$ are each independently hydrogen, halo, $C_{1-4}$alkyl, $C_{1-4}$alkoxy, $C_{1-4}$haloalkyloxy, $C_{1-4}$haloalkyl, $C_{3-7}$alkenyl, amino, carbonyl, nitro, methoxycarbonyl or aminocarbonyl;

Q is O, S or $NR^7$;

X is $CH_2$, O, S, SO or $NR^8$;

Y is O, S or $NR^8$;

n is 0, 1 or 2;

L is $COOR^9$, $CONR^{10}R^{11}$, $C(=S)NR^{10}R^{11}$, CN, or a radical of formula

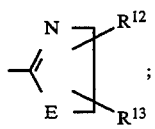

E is O, S or $NR^8$;

$R^7$ is 1,1-dimethyl-2-hydroxyethyl or 2-methyl-2-fluoropropyl;

$R^8$ is hydrogen, $C_{1-6}$alkyl or 1,1-dimethyl-2-hydroxyethyl;

$R^9$ is hydrogen, $C_{1-7}$alkyl, $C_{3-8}$alkenyl, $C_{3-8}$alkynyl, $C_{2-16}$alkyloxyalkyl or $C_{3-7}$cycloalkyl;

$R^{10}$ is hydrogen, $C_{1-3}$alkyl or 1,1-dimethyl-2-hydroxyethyl;

$R^{11}$ is hydrogen, $C_{1-3}$alkyl or phenyl; and $R^{12}$ and $R^{13}$ each independently are hydrogen or methyl. except for:

3,3-diphenyl-3H-furo[3,4-c]pyridin-1-one and 3-(diphenylhydroxymethyl)-N,N-bis(1-methylethyl)-4-pyridinecarboxamide.

2. A compound according to claim 1 wherein $R^1$ and $R^2$ are each independently hydrogen, $C_{1-6}$alkyl or $R^1$ and $R^2$ together with the carbon atom to which they are connected form a spiro $C_{3-6}$cycloalkyl group; Q is O or S; n is 0 or 1; L is $COOR^9$, $CONR^{10}R^{11}$, CN, or a radical of formula

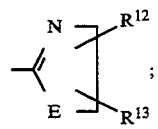

$R^8$ is hydrogen or $C_{1-6}$alkyl; $R^{10}$ is hydrogen or $C_{1-3}$alkyl; $R^{11}$ is hydrogen or $C_{1-3}$alkyl; and $R^{13}$ is hydrogen.

3. A compound according to claim 1 wherein R represents

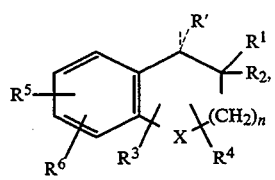

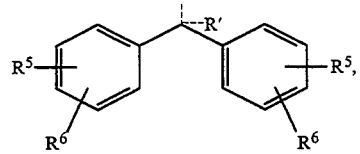

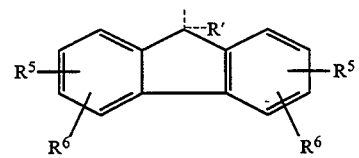

or

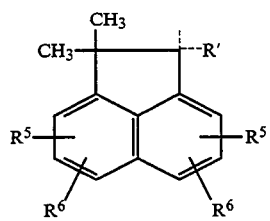

wherein R' is hydrogen, fluoro, hydroxy or a spiro-bond; $R^1$ and $R^2$ are each independently hydrogen, $C_{1-6}$alkyl or $R^1$ and $R^2$ together with the carbon atom to which they are connected form a spiro $C_{3-6}$cycloalkyl group; or R' and $R^1$ form an extra bond; $R^3$ and $R^4$ are each independently hydrogen or $C_{1-6}$alkyl; $R^5$ and $R^6$ are hydrogen; Q is O, S or $NR^7$; X is $CH_2$, O or S; Y is O or $NR^8$; n is 0 or 1; L is $COOR^9$, $CONR^{10}R^{11}$ or $C(=S)NR^{10}R^{11}$; $R^7$ is 1,1-dimethyl-2-hydroxyethyl or 2-methyl-2-fluoropropyl; $R^8$ is hydrogen, $C_{1-6}$alkyl or 1,1-dimethyl-2-hydroxyethyl; $R^9$ is hydrogen or $C_{1-7}$alkyl; $R^{10}$ is hydrogen, $C_{1-3}$alkyl or 1,1-dimethyl-2-hydroxyethyl; and $R^{11}$ is hydrogen, $C_{1-3}$alkyl or phenyl.

4. A compound according to claim 3 wherein R' is hydrogen or a spiro-bond; $R^1$ and $R^2$ are each independently hydrogen or $C_{1-4}$alkyl; $R^3$ and $R^4$ are each independently hydrogen or $C_{1-4}$alkyl; Q is O; X is $CH_2$ or O; Y is O or NH; L is $COOR^9$ or $CONR^{10}R^{11}$; $R^9$ is hydrogen or $C_{1-4}$alkyl; $R^{10}$ is hydrogen or $C_{1-3}$alkyl; and $R^{11}$ is hydrogen or $C_{1-3}$alkyl.

5. A compound according to claim 1 wherein R represents

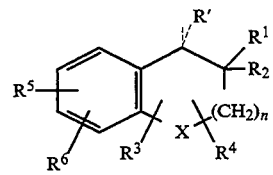

wherein R' is hydrogen or a spiro-bond; $R^1$ and $R^2$ are each independently hydrogen or $C_{1-4}$alkyl; $R^3$ and $R^4$ are each independently hydrogen or $C_{1-4}$alkyl; Q is O; X is $CH_2$; Y is O or NH; and L is $COOCH_3$.

6. A compound according to claim 1 wherein the compound is methyl 3-(2,3-dihydro 2,2-dimethyl-1H-inden-1-yl)-4-pyridinecarboxylate.

7. A method for controlling weeds, which method comprises applying to said weeds or to the locus thereof a herbicidally effective amount of a compound as claimed in claim 1.

8. A method for controlling weeds, which method comprises applying to said weeds or to the locus thereof a herbicidally effective amount of a compound as claimed in claim 2.

9. A method for controlling weeds, which method comprises applying to said weeds or to the locus thereof a herbicidally effective amount of a compound as claimed in claim 3.

10. A method for controlling weeds, which method comprises applying to said weeds or to the locus thereof a herbicidally effective amount of a compound as claimed in claim 4.

11. A method for controlling weeds, which method comprises applying to said weeds or to the locus thereof a herbicidally effective amount of a compound as claimed in claim 5.

12. A method for controlling weeds, which method comprises applying to said weeds or to the locus thereof a herbicidally effective amount of a compound as claimed in claim 6.

13. A method according to claim 7 for selectively controlling weeds in crops of useful plants.

14. A method according to claim 8 for selectively controlling weeds in crops of useful plants.

15. A method according to claim 9 for selectively controlling weeds in crops of useful plants.

16. A method according to claim 10 for selectively controlling weeds in crops of useful plants.

17. A method according to claim 11 for selectively controlling weeds in crops of useful plants.

18. A method according to claim 12 for selectively controlling weeds in crops of useful plants.

19. A herbicidal composition comprising one or more inert carriers and, if desired, other adjuvants, and as active ingredient a herbicidally effective amount of a compound as claimed in claim 1.

20. A herbicidal composition comprising one or more inert carriers and, if desired, other adjuvants, and as active ingredient a herbicidally effective amount of a compound as claimed in claim 2.

21. A herbicidal composition comprising one or more inert carriers and, if desired, other adjuvants, and as active ingredient a herbicidally effective amount of a compound as claimed in claim 3.

22. A herbicidal composition comprising one or more inert carriers and, if desired, other adjuvants, and as active ingredient a herbicidally effective amount of a compound as claimed in claim 4.

23. A herbicidal composition comprising one or more inert carriers and, if desired, other adjuvants, and as active ingredient a herbicidally effective amount of a compound as claimed in claim 5.

24. A herbicidal composition comprising one or more inert carriers and, if desired, other adjuvants, and as active ingredient a herbicidally effective amount of a compound as claimed in claim 6.

* * * * *